(12) United States Patent
Al-Oboudi

(10) Patent No.: US 7,771,332 B1
(45) Date of Patent: Aug. 10, 2010

(54) SHOULDER STABILIZER ORTHOTIC DEVICE

(76) Inventor: Waleed Al-Oboudi, 4806 Via El Sereno, Torrance, CA (US) 90505

( * ) Notice: Subject to any disclaimer, the term of this patent is extended or adjusted under 35 U.S.C. 154(b) by 0 days.

(21) Appl. No.: 11/241,784

(22) Filed: Sep. 30, 2005

Related U.S. Application Data

(60) Provisional application No. 60/615,221, filed on Oct. 1, 2004.

(51) Int. Cl.
*A63B 23/00* (2006.01)
*A61F 5/00* (2006.01)
*A61F 5/37* (2006.01)

(52) U.S. Cl. .......................... 482/148; 602/20; 128/878

(58) Field of Classification Search ................ 482/124, 482/139, 148; 473/207, 212–3, 450, 518, 473/213; 602/20, 4, 5, 12, 16; 128/874, 128/877–8, 878; 2/44, 45; 42/94; 70/16–18
See application file for complete search history.

(56) References Cited

U.S. PATENT DOCUMENTS

| | | | | |
|---|---|---|---|---|
| 2,560,243 A * | 7/1951 | Peterson | .......................... | 602/4 |
| 3,069,169 A * | 12/1962 | Topping | ..................... | 473/212 |
| 3,390,477 A * | 7/1968 | Galbraith | ........................ | 42/94 |
| 3,804,420 A * | 4/1974 | Boyd | .......................... | 473/212 |
| 3,814,419 A * | 6/1974 | Bjorklund et al. | ........... | 482/124 |
| 4,383,685 A * | 5/1983 | Bishop | ........................ | 473/450 |
| 4,417,569 A * | 11/1983 | Brudny | .......................... | 602/20 |
| 4,660,829 A * | 4/1987 | Whiteneir | ..................... | 473/63 |
| 4,716,895 A * | 1/1988 | Marques et al. | ................. | 602/4 |
| 4,751,923 A * | 6/1988 | Marino | ........................... | 602/4 |
| 5,295,690 A * | 3/1994 | Johnson | ....................... | 473/212 |
| 5,385,536 A * | 1/1995 | Burkhead et al. | ............. | 602/20 |
| 5,628,725 A | 5/1997 | Ostergard | | |
| 5,665,058 A * | 9/1997 | Young | .......................... | 602/20 |
| 5,934,281 A * | 8/1999 | Brocher | ...................... | 128/869 |
| 6,009,655 A * | 1/2000 | Austin | ........................... | 42/94 |
| 6,196,931 B1* | 3/2001 | Wilt | ........................... | 473/212 |
| 6,283,877 B1* | 9/2001 | Cook | .......................... | 473/450 |
| 6,398,746 B2 | 6/2002 | Bramlage et al. | | |
| 6,595,936 B1* | 7/2003 | Oladipo | .......................... | 602/4 |
| 2003/0073941 A1* | 4/2003 | Betz | ............................... | 602/5 |

* cited by examiner

*Primary Examiner*—Loan Thanh
*Assistant Examiner*—Allana Lewin
(74) *Attorney, Agent, or Firm*—Knobbe, Martens, Olson & Bear, LLP

(57) ABSTRACT

An orthotic device designed to prevent shoulder injuries in individuals suffering from muscle spasticity, weakness of muscle, and other symptoms of neurological disorders is disclosed. The device includes a lower arm support configured to receive and position an individual's lower forearm or wrist adjacent to the individual's body in a manner so as to stabilize the shoulder. The device further includes an attachment mechanism configured to attach to a person's body via a belt or article of clothing. The support and attachment mechanism are interconnected in a manner that permits the person's arm to be positioned adjacent the body in a fixed position so as to substantially minimize movement of the shoulder. In certain implementations, the device further includes a static adjustment portion which allows the positioning of the first portion to be adjusted relative to the second portion.

5 Claims, 3 Drawing Sheets

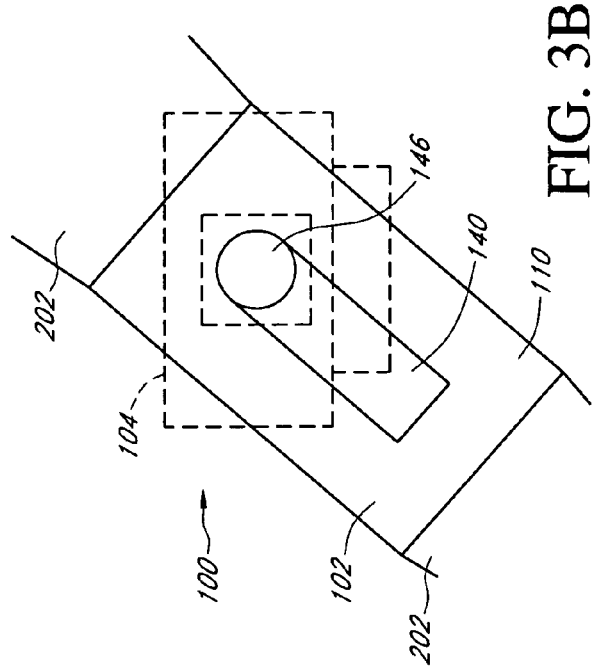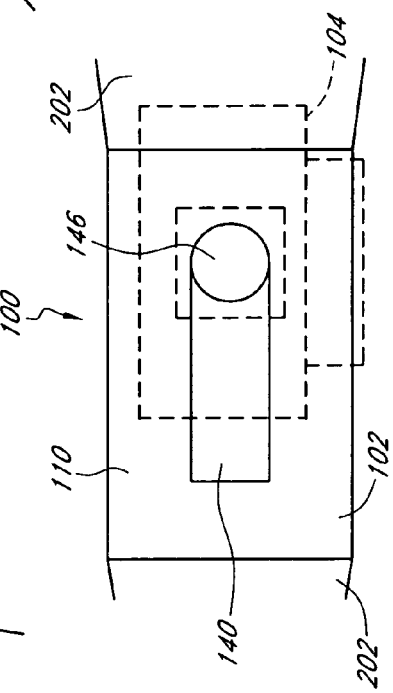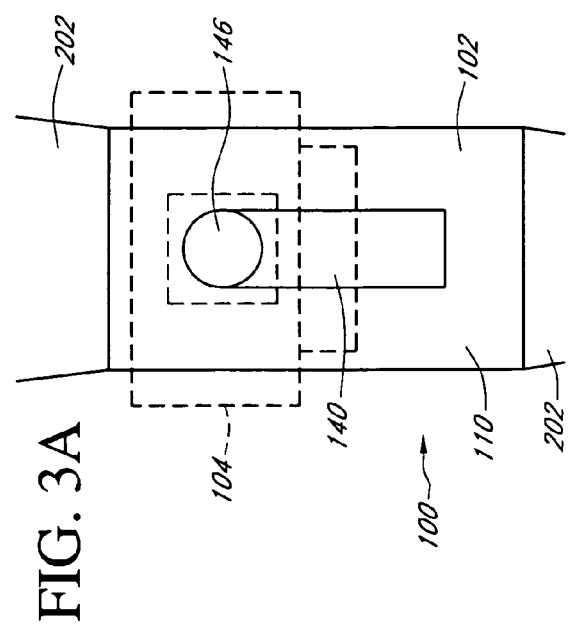

SHOULDER STABILIZER ORTHOTIC DEVICE

RELATED APPLICATIONS

This application claims the benefit of priority under 35 U.S.C. §119(e) of U.S. Provisional Application No. 60/615,221 filed on Oct. 1, 2004 and entitled SHOULDER STABILIZER ORTHOTIC DEVICE, the entirety of which is incorporated herein by reference.

BACKGROUND OF THE INVENTION

1. Field of the Invention

The present invention relates generally to orthotic devices and, in particular, concerns an orthotic device for use in providing shoulder stability and substantially preventing shoulder separation or partial dislocation in individuals suffering from muscle spasticity, weakness of muscle, and other symptoms of neurological disorders.

2. Description of the Related Art

Patients with neurological disorders often suffer from muscle spasticity and weakness of muscle, which are usually caused by damage to the systems that control voluntary muscle movements. Spasticity is demonstrated when muscles receive improper nerve signals causing them to involuntarily contract. In weakness of muscle, the systems which control motor function are damaged, resulting in paralysis and degeneration of muscle. Improper control of brain signals is often due to damage within the brain caused by stroke, brain injury, or other traumas.

Injuries such as shoulder separation and partial shoulder dislocation are common consequences of muscle spasticity and weakness of muscle. In shoulder separation, the ligaments which connect the collarbone and shoulder blade are partially or completely torn, while in partial dislocation, the rounded top of the upper arm bone slips partially out of position with respect to the joint it normally rests within. These shoulder injuries are potentially painful and disabling, requiring medical treatment ranging from bracing and physical therapy in mild cases, to surgery in the most severe.

In view of the foregoing, there is need for an orthotic device for use in preventing shoulder injuries in patients suffering from muscle spasticity, weakness of muscle, and other neurological disorders. To this end, there is a particular need for an orthotic device which provides constrains movement of a patient's arm and provides shoulder stability.

SUMMARY OF THE INVENTION

An embodiment provides a shoulder stabilizing device for substantially preventing shoulder separation or partial shoulder dislocation in individuals suffering from muscle spasticity, weakness of muscle, or other neurological disorders. The device includes a first portion configured to receive and position an individual's lower forearm arm or wrist adjacent to the individual's body in a manner so as to stabilize the shoulder. The device further includes a second portion configured to attach to the individual's body via a belt or article of clothing. The first and second portions are interconnected in a manner that permits the individual's arm to be positioned adjacent the body in a fixed position so as to substantially minimize movement of the shoulder. Preferably, the device further includes a pivotable joint which allows the positioning of the first portion to be adjusted relative to the second portion.

BRIEF DESCRIPTION OF THE DRAWINGS

FIG. 3 is a side view of the shoulder stabilizer orthotic device of one preferred embodiment illustrating the pivoting capability of the lower support portion along an axis extending outward from the joint portion.

DETAILED DESCRIPTION OF THE PREFERRED EMBODIMENT

Figure 1:
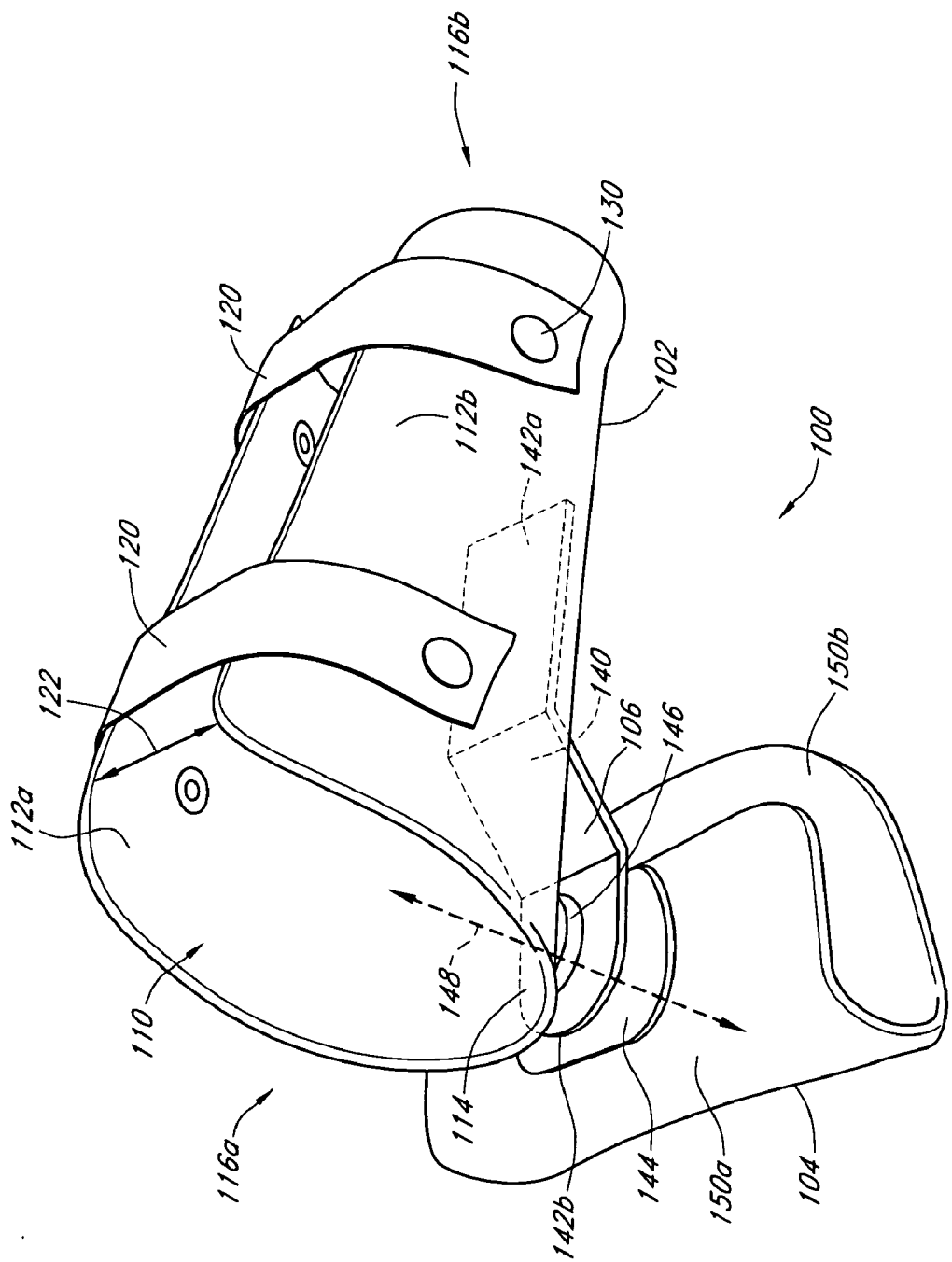
FIG. 1 is a perspective view of a shoulder stabilizer orthotic device of one preferred embodiment.

FIG. 1 illustrates a perspective view of the shoulder stabilizer orthotic device 100. Generally, the device 100 is designed to affix the position of a patient's shoulder relative to their body so as to substantially prevent partial dislocation or shoulder dislocation due to muscle spasticity, weakness of muscle, or other disorders. The device 100 includes a lower arm support 102, an attachment portion 104, and a joint portion 106 which connects the lower arm support 102 to the attachment portion 104.

The lower arm support 102 possesses a generally tubular, U-shaped support portion 110, comprising left and right facing sidewalls 112a and 112b, a bottom facing wall 114, and a first end 116a and a second end 116b. The support portion 110 is preferably dimensioned so to allow the placement of at least a portion of a patient's forearm within the contour of the support portion 110, surrounded by the walls 112a, 112b, and 114 on three sides. These walls 112a, 112b, and 114 are substantially smooth, configured to engage with a patient's arm in a manner to be described in more detail below in respect to FIG. 2. The sidewalls 112a and 112b are tapered from the first end 116a to the second end 116b. As the human forearm becomes wider towards the elbow and a patient's arm is inserted into the support portion 110 at the first end 116a, the tapered shape of the support portion 110 promotes accommodation of a patient's arm within the device 100.

Also shown in the embodiment of FIG. 1 is a plurality of restraining straps 120. The straps 120 are generally rectangular in shape and of sufficient length to span the mouth 122 of the support portion 110. In one embodiment, the lower arm support 102 has snaps or other strap securing devices 130 incorporated into the straps 120 and the support portion 110 so to allow attachment and separation of the straps 120 to the left and right sidewalls 112a and 112b of the support portion 110. These straps 120 allow the lower arm support 102 to be fit to the size of a patient's arm in a manner to be described in greater detail in respect to FIG. 2.

It will be appreciated that the support portion 110 design illustrated is simply one embodiment and that a number of variations of this design may be made by those skilled in the art without departing from the scope of the present teachings. In one aspect, the first and second ends 116a and 116b of the support portion 110 of the shoulder stabilizer orthotic device 100 may be rounded in order to substantially reduce any sharp edges which may cause injury to the patient during use of the orthotic device 100. In another aspect, the lower arm support 102 may be constructed in a non-tubular geometry without departing from the scope of the present teaching.

FIG. 1 further illustrates the joint portion 106 which connects the lower arm support 102 to the attachment portion 104. In one embodiment, the joint portion 106 is comprised of an attachment arm 140 which is attached to the lower arm support 102 at a first end 142a, a joint anchor plate 144 which is attached to the attachment portion 104 and mates with a second end 142b of the attachment arm 140, and an adjustment device 146 which secures the second end 142b of the attachment arm 140 to the anchor plate 144 and is used to adjust the position of the lower arm support 102 relative to the attachment portion 104. In the embodiment of FIG. 1, the adjustment device 146 may comprise a screw other device that can be loosened so to allow the lower arm support 102 to rotate relative to the patient's body to a desired position. The rotational adjustment process is described in more detail below in respect to FIGS. 3A-3C.

The attachment portion 104 is also illustrated in FIG. 1. The attachment portion 104 is configured to engage with an article of clothing worn by a patient. In one embodiment, the attachment portion 104 comprises a U-shaped clip having a joint side 150a and a patient side 150b. The attachment portion 104 is configured to attach to a patient's belt or panty waist line to secure the orthotic device 100 to the patient, as described below in respect to FIG. 2.

Figure 2:
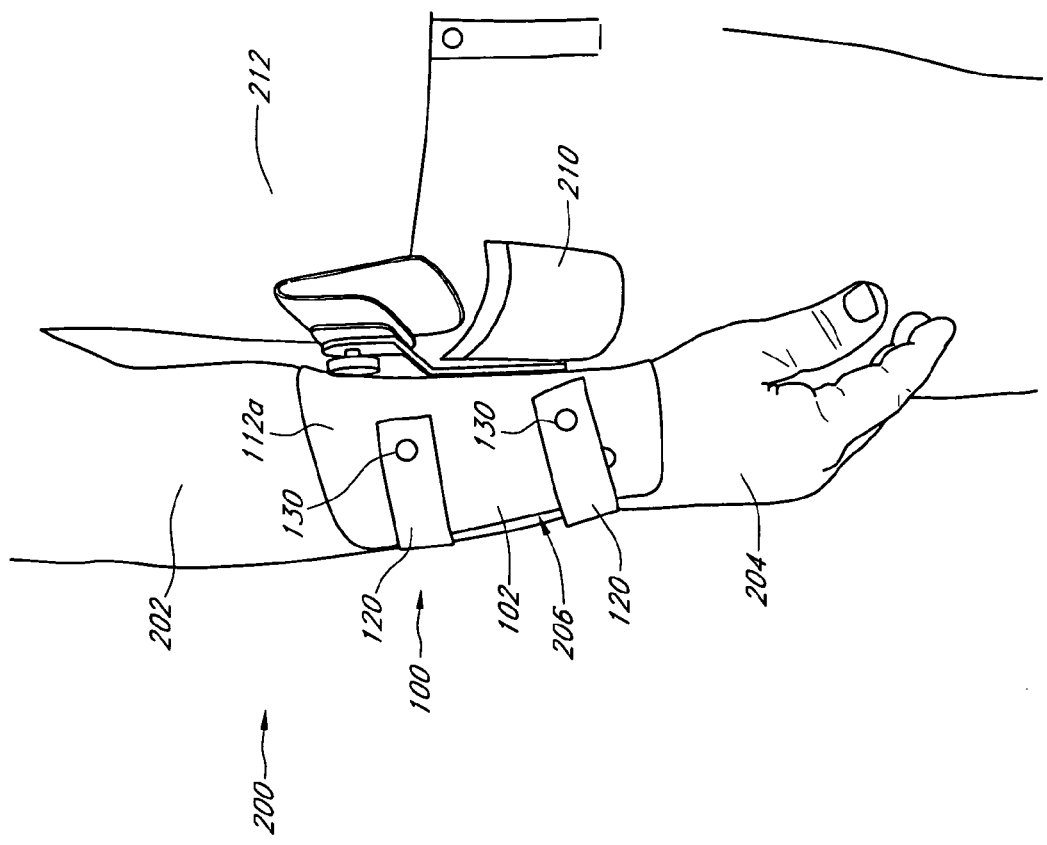
FIG. 2 illustrates a manner in which the shoulder stabilizer orthotic device of FIG. 1 can be used.

FIG. 2 illustrates a perspective view of the orthotic device 100 in use by a patient 200. The patient's arm 202 is inserted into the lower arm support 102, hand 204 first until the lower arm support 102 substantially surrounds the forearm 206. The straps 120 are attached to one of the walls 112a and 112b of the support portion 110 and are drawn taut across the mouth 122 of the support portion 110 and fixed in place using the strap securing device 130. In this manner, the patient's arm 202 is fixed within the lower arm support 102 until the straps 120 are released.

FIG. 2 also shows how the attachment portion 104 can be inserted into an article of clothing on the patient such as a pocket, belt, or pant waist line. The attachment portion secures around a pocket 210, which inhibits the interconnected lower arm support 102 from moving. Thus, the patient's arm 202 is substantially immobilized in a position that largely prevents movement of the shoulder, which in turn reduces the likelihood of shoulder separation or partial shoulder dislocation caused by involuntary muscle movement.

FIGS. 3A-3C illustrate the process by which the lower arm support 102 may be pivoted with respect to the attachment portion 104. FIGS. 3A-3C illustrate a cross-sectional view of the orthotic device 100 facing the mouth 122 of the support portion 110 during the process of pivoting the lower arm support 102. In the first position of FIG. 3A, the lower arm support 102 containing a patient's arm 202 is pointed downward, and the attachment portion 104 is secured to the patient 200 in the manner described above with respect to FIG. 2. The adjustment device 146 is loosened to allow the lower arm support 102 to rotate while the attachment portion 104 remains fixed to the body. Once the lower support portion 102 is adjusted to the desired position, the adjustment device 146 can be tightened so as to affix the position of the lower support portion 102. Reversing the sequence of Figures from 3C-3A returns the orthotic device 100 to its original position.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others.

What is claimed is:

1. An orthotic device for providing shoulder stability in individuals suffering from neurological disorders, comprising:
   a lower arm support configured to receive a portion of an individual's lower forearm, said lower arm support is configured to allow the placement of the portion of the individual's forearm within the contour of the lower arm support wherein the lower arm support is configured to maintain an individual's arm substantially straight and parallel to a longitudinal axis of the individual's body;
   an attachment portion comprising a U-shaped clip that is disposed adjacent the lower arm support and configured to attach the device to the individual's body via a belt or pant waistline in a manner so as to substantially immobilize the individual's forearm in a position adjacent and substantially parallel to the longitudinal axis to the individual's body, the individual's body which substantially prevents movement of the individual's shoulder;
   a pivotable joint interconnecting the lower arm support and the attachment portion, said pivotable joint comprises an attachment arm having a first end and a second end, a joint anchor plate, and an adjustment device, wherein the first end of the attachment arm is attached to the lower arm support and the second end of the attachment arm mates with the joint anchor plate, wherein the joint anchor plate is attached to the attachment portion, wherein the adjustment device secures the second end of the attachment arm to the joint anchor plate and is adapted to adjust the position of the lower arm support relative to the attachment portion to a desired position, wherein the adjustment device is configured to be tightened so as to affix the position of the lower arm support to the desired position.

2. The orthotic device of claim 1, wherein the adjustment device comprises a screw that can be loosened so as to allow the lower arm support to rotate relative to the individual's body to a desired position.

3. The orthotic device of claim 1, wherein the lower arm support comprises a tubular support portion, left and right facing sidewalls, and a bottom facing wall.

4. The orthotic device of claim 1, further comprising straps adapted to retain the portion of the forearm in the lower arm support.

5. The orthotic device of claim 1, wherein the lower arm support and the attachment portion are pivotable about the pivotable joint.

* * * * *